United States Patent [19]
Boetzkes

[11] Patent Number: 5,324,314
[45] Date of Patent: Jun. 28, 1994

[54] METHOD AND APPARATUS FOR CAPACITIVELY REGENERATING TISSUE AND BONE

[76] Inventor: Peter C. Boetzkes, 888 Shakespeare Avenue, North Vancouver, B.C. V7K 1E6, Canada

[21] Appl. No.: 856,838

[22] Filed: Mar. 23, 1992

Related U.S. Application Data

[63] Continuation of Ser. No. 717,071, Jun. 18, 1991, abandoned, which is a continuation of Ser. No. 188,337, Apr. 29, 1988, Pat. No. 5,038,780.

[51] Int. Cl.$^5$ .................................................. A61N 1/40
[52] U.S. Cl. ......................................... 607/51; 607/50; 607/76
[58] Field of Search ............... 128/419 F, 422, 82.1, 128/901; 600/13, 14; 607/50, 51, 52, 62, 63, 64, 76

[56] References Cited

U.S. PATENT DOCUMENTS

| | | | |
|---|---|---|---|
| 3,915,151 | 10/1975 | Kraus | 128/419 R |
| 4,289,134 | 9/1981 | Bernstein | 128/419 PG |
| 4,315,503 | 2/1982 | Ryaby et al. | 128/419 F |
| 4,414,979 | 11/1983 | Hirshorn et al. | 128/419 F |
| 4,432,361 | 2/1984 | Christensen et al. | 128/419 F |
| 4,436,093 | 3/1984 | Belt | 128/419 PG |
| 4,459,998 | 7/1984 | Dugot | 128/419 F |
| 4,600,010 | 7/1986 | Dugot | 128/419 F |
| 4,665,920 | 5/1987 | Campbell | 128/419 F |
| 4,674,482 | 6/1987 | Walton et al. | 128/419 F |
| 4,846,178 | 7/1989 | Fuxue et al. | 128/419 F |

OTHER PUBLICATIONS

Burns et al, Principles of Electronic Circuits, W. C. Brown Pub. Co., Dec. 1984, pp. 15-74-15-80.

Primary Examiner—William F. Kamm
Assistant Examiner—Kennedy J. Schaetzle

[57] ABSTRACT

A system (10) is disclosed for facilitating the healing of traumatized tissue and broken or fractured bone. The system (10) establishes an electric field between a pair of electrodes (14) positioned on opposite sides of the patient site (12), resulting in the production of an alternating current having the desired frequency and amplitude characteristics in the tissue or bone. Specifically, the system (10) includes a resonator (32) formed by an inductor (36) coupled in series with the resistor (R1) and capacitor (C1) of an equivalent circuit (34) representing the patient site (12), the electrodes (14), and any gaps (30) therebetween. This resonator (32) also includes a capacitor (C2) designed to prevent spurious, high-frequency oscillations. The resonator (32) is operated by a free-running oscillator (16), which maintains the operation of the resonator (32) at its resonant frequency. The oscillator (16) includes a forward network (38), having a CMOS inverter (42), and a feedback network (40), including an open-loop operational amplifier (52), and provides a simple, stable, and efficient form of operation free from spurious, high-frequency oscillations.

11 Claims, 3 Drawing Sheets

METHOD AND APPARATUS FOR CAPACITIVELY REGENERATING TISSUE AND BONE

This application is a continuation application based on prior copending application Ser. No. 07/717,071, filed on Jun. 18, 1991, now abandoned, which, in turn, was a continuation of prior application Ser. No. 07/188,337, filed Apr. 29, 1988, now U.S. Pat. No. 5,038,780, the benefit of the filing dates of which are hereby claimed under 35 U.S.C. § 120.

FIELD OF THE INVENTION

This invention relates generally to the electric stimulation of tissue and bone and, more particularly, to the production of a stimulative electric current in the tissue or bone via a capacitively established electric field.

BACKGROUND OF THE INVENTION

The use of electric current to facilitate the healing of traumatized tissue and broken or fractured bone has been recognized for some time. The stimulative effect of such current appears to occur whether the flow of current is induced naturally, by internal body mechanisms, or artificially, by external sources. While the natural flow of current produced by electrochemical, myoelectric, and piezoelectric-like body mechanisms advantageously facilitates healing without external circuitry, is some instances it is desirable to expedite the recuperative process by artificially supplementing the natural current flow.

A variety of different techniques have been devised for establishing supplemental electric currents in tissue and bone. Briefly, such techniques can be grouped according to both the type of current developed and the manner in which the current is established. Considering first the type of current product, the current may be characterized as either a direct (DC) current, having an amplitude that is substantially constant as a function of time, or an alternating (AC) current, which exhibits a time-dependent amplitude variation. The use of AC current is preferred because it can be established in a variety of ways, discussed below. DC current, on the other hand, can be induced only by providing a direct electrical connection between the tissue or bone and the energy source.

The manner in which the auxiliary stimulating current is induced offers several alternative forms of classification. First, such techniques can be categorized as being either invasive or noninvasive, depending on the connections provided to the patient. Invasive techniques involve the application of electric current directly to the site of the trauma or fracture through electrodes implanted at the site. While this approach minimizes the electric potential required to generate a particular desired current in the tissue or bone, it also involves the expense and risk of infection attendant surgical implantation procedures. As a result, noninvasive procedures, in which the flow of electric current in the tissue or bone is induced by apparatus external to the patient, are preferred.

The noninvasive establishment of an AC current in tissue or bone can be further grouped according to the electric principle involved in its production. For example, a resistive approach involves the conduction of current directly to the patient through special electrodes coupled to the patient's skin via conductive gel. This technique has the disadvantage of requiring good electrical contact between the electrodes and the skin, necessitating the periodic replacement of the conductive gel on the electrodes.

A second, or inductive, approach employs magnetic fields to establish the desired AC current in the tissue or bone. Specifically, this approach involves the application of an electric current to magnetic coils positioned proximate the patient. The flow of current through the coils produces a magnetic field in the patient's bone or tissue, resulting in the establishment of the desired alternating therapeutic current. This approach has a number of disadvantages including the required use of bulky magnetic coils and an energy source having an output whose frequency and waveform are sufficient to induce the desired stimulating currents at the patient site. The inductive approach also involves relatively large energy losses attributable to the heating of the coil windings produced by the flow of current therethrough.

The third technique for noninvasively establishing an alternating current in the patient's tissue or bone can be referred to as the "capacitive" or electric field approach. This technique typically employs a pair of electrodes that are placed on opposite sides of the treatment site and are insulated from the patient's skin. Energy applied to the electrodes establishes an electric field between the electrodes, normal to the skin. It is this electric field that induces the alternating therapeutic current at the treatment site.

While this approach overcomes the difficulties outlined above with respect to the resistive and inductive techniques, the capacitive production of therapeutically effective levels of electric current at the patient treatment site traditionally presents several additional problems. For example, the patient's skin normally contributes a series capacitive reactance to the equivalent electric circuit representative of the elements between the electrodes. In addition, a much larger variable capacitive reactance is exhibited by the insulative, dielectric "gaps" between the electrodes and the patient.

The combined series capacitive reactance of the elements between the electrodes has been a problem for several reasons. First, this reactive component seriously attenuates the current flow produced by a given potential applied to the electrodes. To understand how this energy loss arises, it may be helpful to briefly review the dynamics of interaction between the stimulating current and the patient. To be therapeutically effective, the electric current must have a frequency that is low enough to ensure its penetration to the site of the fracture or trauma. This requirement is imposed because a high-frequency current will concentrate near the dermal region of the patient in response to a mechanism known as the "electromagnetic skin effect." Other, biological, mechanisms that limit the efficacy of relatively high-frequency current also likely exist.

At therapeutically effective frequencies, the peak energy stored electrostatically in both the electrode-to-skin interface and the epidermis during one cycle of the alternating voltage potential applied to the electrodes is substantially larger than the energy absorbed by the tissue and bone being treated. This stored energy is typically either dissipated within the source or radiated as electromagnetic energy, resulting in a system inefficiency or energy loss. As a result, high levels of reactive power are required to establish the desired therapeutic current.

As an alternative to the use of higher voltages to compensate for energy losses, an inductive reactance can be employed to produce a resonant circuit that reduces the energy losses. For example, a series-connected inductor can be used to recapture the stored energy and apply it to the treatment site during the next cycle of the alternating voltage applied to the electrodes. As a result, only a relatively small amount of energy is dissipated and radiated.

Even with energy losses reduced, the capacitive technique of establishing therapeutic current in tissue and bone still presents several problems. As noted previously, the capacitive reactance exhibited by the dielectric gaps between the electrodes and the patient represents a rather large and variable electrical impedance to the drive circuit. The addition of the inductor to form a resonant circuit having a high quality factor Q, provides a significant reduction in impedance when the circuit is operated at its resonant frequency. Because the capacitive portion of the circuit may vary substantially in response to both the condition of the patient and movement between the electrodes and patient, when a fixed inductance is employed the circuit can be maintained at resonance only by adjusting the frequency of the driver to correspond to the resonant frequency of the circuit as it varies with the changing capacitance. Alternatively, a variable inductive reactance can be used to negate the effect of the changes in capacitance, leaving the resonant frequency of the circuit unchanged.

In U.S. Pat. No. 4,459,988 (Dugot) a circuit is disclosed that employs the former technique. Specifically, a portion of the patient positioned between stimulating electrodes is included in a series resonant circuit incorporating positive feedback to maintain the frequency of the stimulating signal at the resonant frequency of the circuit. The Dugot approach, however, suffers from several disadvantages. First, the disclosed implementation is relatively complex and involves a large number of components. Positive feedback is required to stabilize the circuit with respect to frequency and automatic gain control is preferably employed to regulate the amplitude of the signal generator's output. In addition, the output produced by the circuit may be subject to spurious and multiple high-frequency oscillations decreasing the efficiency of the system. The use of a variable inductive reactance to maintain a constant resonant frequency in the presence of capacitive changes disadvantageously requires the use and expense of some form of adjustable inductor and feedback to control it.

In light of the preceding remarks, it would be desirable to provide a method and apparatus for noninvasively establishing a regenerative electric current in traumatized tissue and broken or fractured bone. It would further be desirable to employ a capacitive technique of establishing such a current that is simple, does not require a high-voltage potential to overcome large variable gap capacitances, is inherently stable with respect to both frequency and amplitude, and rejects high-frequency spurious oscillations.

SUMMARY OF THE INVENTION

In accordance with this invention, a method and apparatus are provided for capacitively establishing an alternating electric field between a pair of stimulation electrodes. The electrodes are typically separated by a patient region that includes traumatized tissue and/or broken or fractured bone and by dielectric gaps between the electrodes and the patient. The electric field is designed to produce an alternating current in the tissue or bone to accelerate healing and is established by a free-running oscillator. Oscillation is maintained with the aid of a resonator that includes an inductor and the resistive and capacitive components provided by the patient, electrodes, and gaps. The oscillator has a simple construction, designed to operate in an amplitude and frequency-stable manner, with its frequency of oscillation tracking changes in the resonant frequency of the resonator attributable to, for example, variations in the capacitance of the dielectric gaps. The oscillator is further constructed to limit the occurrence of spurious high-frequency oscillations.

In accordance with a particular aspect of this invention, an apparatus is provided for applying an electric current to a region of a patient through a pair of electrodes positionable in noncontacting relationship with respect to the patient. This region of the patient, and any gaps between the patient and the electrodes, exhibits a series capacitance and resistance. The apparatus includes an inductor, coupled to one of the electrodes to define a resonator in cooperation with the series capacitance and resistance. An oscillator is coupled to the inductor to provide to the resonator a periodic current having a frequency that is substantially equal to the resonant frequency of the resonator. Finally, an element is included to limit the occurrence of spurious oscillation frequencies in the periodic current provided by the oscillator.

In accordance with another aspect of this invention, an apparatus is provided for establishing an electric field between a pair of electrodes separable by a gap that exhibits a series capacitance and resistance. The apparatus includes an inductor connectable in series with one of the electrodes to define a resonant circuit with the series capacitance and resistance. A low-impedance voltage source is included to apply a square wave output, shifted in phase by approximately 180 degrees from the source input, to one of the electrodes. The other one of the electrodes is coupled to the input of an open-loop operational amplifier whose output is coupled to the voltage source. The operational amplifier has a gain sufficient to provide a unity gain for the apparatus and produces a phase shift sufficient to provide a zero-degree phase shift for the apparatus.

BRIEF DESCRIPTION OF THE DRAWINGS

The invention will presently be described in greater detail by way of example, with reference to the accompanying drawings, wherein.

DETAILED DESCRIPTION OF THE PREFERRED EMBODIMENT

Figure 1:
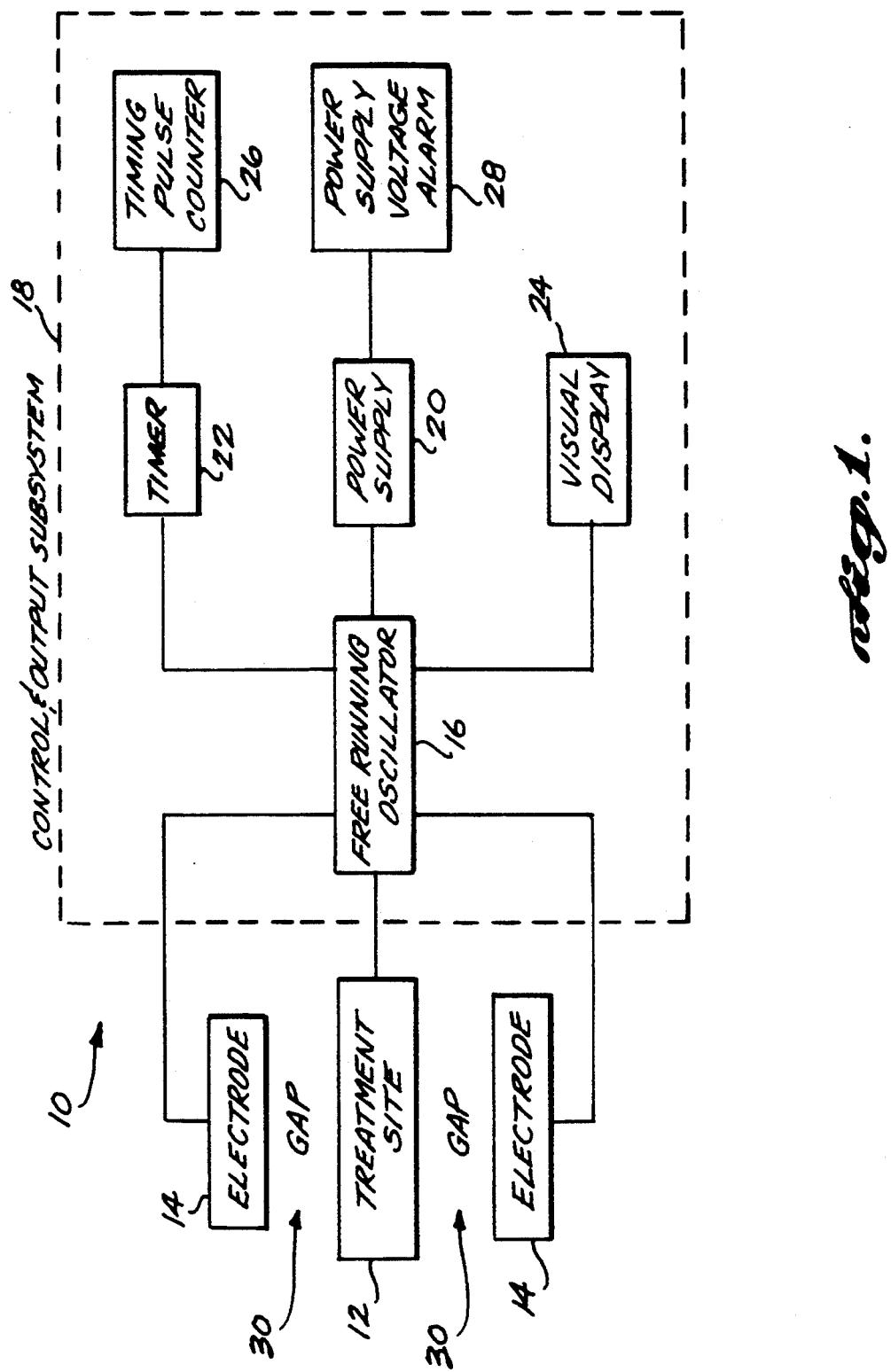
FIG. 1 is a block diagram of a system, constructed in accordance with this invention, that capacitively regenerates the tissue and bone of a patient.

Referring now to FIG. 1, a system 10 for facilitating the healing of traumatized tissue and broken or fractured bone is illustrated. The system 10 establishes an alternating electric current at a treatment site 12, which includes the bone and tissue for which enhanced regeneration is desired. As discussed in greater detail below, this therapeutic current is induced by the establishment of an electric field between a pair of electrodes 14 positioned on opposite sides of the site 12. A free-running oscillator 16, included in a control and output subsystem 18, provides the energy required to maintain the field between electrodes 14. Oscillator 16 is powered by a supply 20 and is controllably activated and deactivated in response to a timer 22. A visual display 24, included in subsystem 18, provides an output indicating that a therapeutic current is flowing at the treatment site 12. As additional outputs, subsystem 18 includes a timing pulse counter 26 to provide information concerning the length of time during which therapeutic current is applied to the site 12 and an alarm 28 that indicates that supply 20 is no longer able to sustain the desired operation of oscillator 16.

While the operation of system 10 is described in greater detail below, its primary function is to establish a therapeutic current at site 12. In the preferred arrangement, an alternating therapeutic current of approximately 5 milliamperes is produced. The frequency of the alternating current is a function of a variety of factors, including the structure of site 12, electrodes 14, and free-running oscillator 16, as well as the relative position of site 12 and electrodes 14.

While a therapeutic effect is produced by induced currents having a relatively wide range of frequencies, the current's frequency should be sufficiently high to prevent the deleterious electromigration of isotopes or ionic species at the treatment site 12. On the other hand, because a "conductor" such as site 12 exhibits a "skin effect" at high frequencies that cause current to concentrate near the surface of the conductor, the frequency must be sufficiently low to ensure that current is induced, for example, in the fracture of a bone lying well beneath the surface of the patient's skin. It has been found that the establishment of an alternating current with a nominal frequency of approximately 50 kilohertz provides the desired therapeutic effect for all normally expected patient and electrode conditions and ensures that the frequency will remain within an acceptable range as the oscillator 16 responds to varying patient and electrode conditions.

Turning now to a more detailed discussion of the various components of system 10, the electrodes 14 are constructed to satisfy a variety of operating criteria. For example, because the current-inducing electric field is established normal to the surface of electrodes 14, the area of electrodes 14 directly affects the cross-sectional area of the treatment site 12 in which a therapeutic current is produced. In addition, the construction details of electrodes 14, including their size and the materials employed, will influence the capacitive reactance introduced by the electrodes. In the preferred arrangement, electrodes 14 are circular plates of conductive elastomer, such as carbon-filled silicone rubber, having a diameter of 8 cm, a thickness of 0.1 cm, and a typical capacitance of 50 pF.

As indicated in the block diagram of FIG. 1, the electrodes 14 are preferably spaced apart from the treatment site 12 by gaps 30. The gaps 30 can be physically maintained by the inclusion of a rigid dielectric material between the electrodes 14 and site 12. For example, in a preferred arrangement, the electrodes 14 are embedded in a cast that surrounds the traumatized tissue and broken or fractured bones. The gaps 30 then include both the dielectric cast material and any air gap interposed between electrodes 14 and the treatment site 12 of the patient. Because the length of the air gaps will likely vary substantially in response to, for example, patient movement, the equivalent capacitive reactance of the circuit may undergo significant variations. It is these variations that the free-running oscillator 16 is designed to compensate for, resulting in the production of an acceptable therapeutic current at the site 12 under all normally expected conditions.

Figure 2:
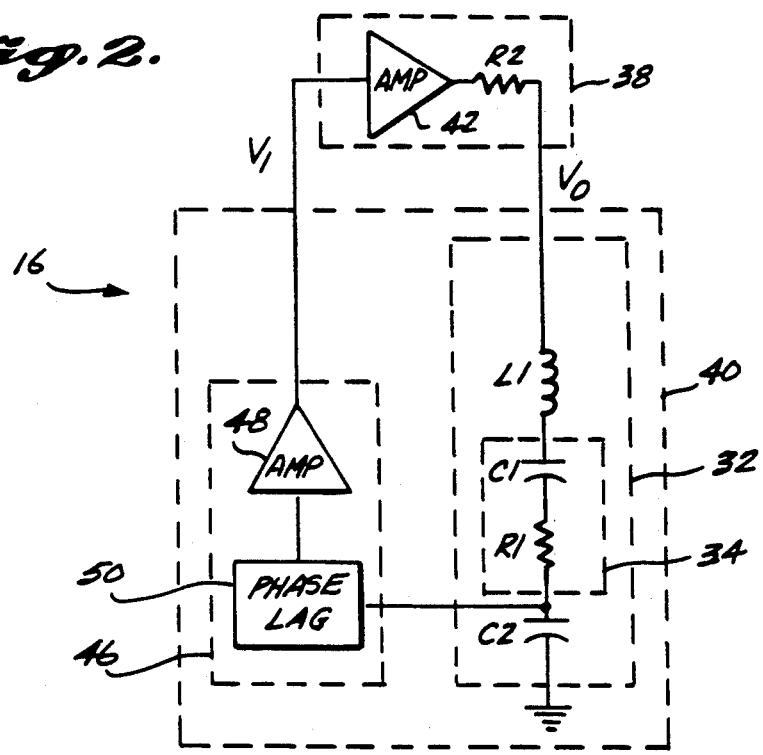
FIG. 2 is a schematic diagram of a an oscillator circuit, employed by the system of FIG. 1, which provides a periodic current to the patient through a pair of electrodes separated from the patient by gaps.

Turning now to a more detailed discussion of the free-running oscillator 16, reference is had to FIG. 2. As shown, the oscillator 16 operates in connection with a series resonant circuit or resonator 32 defined by an equivalent site circuit 34 and an inductor L1. The equivalent circuit 34 includes a resistive component R1 and a capacitive component C1 that are representative of site 12, electrodes 14, and gaps 30. As discussed in greater detail below, the oscillator 16 is constructed to ensure that its operating frequency precisely tracks the changing resonant frequency of resonator 32. Oscillator 16 is further constructed from a minimum of components, providing a stable level of injected current over a desired frequency range without the introduction of high-frequency spurious oscillations.

As noted, free-running oscillator 16 is designed to operate resonator 32 at its resonant frequency. Resonance is, by definition, the condition in which the impedance of the resonator 32 is purely resistive, causing the voltage and current at the input of resonator 32 to be in phase. Because the inductive and capacitive components L1 and C1 do not affect the current flowing through resonator 32 in this condition, the magnitude of the current is a function only of the voltage applied to resonator 32 and the resistance of resonator 32.

To ensure that the free-running oscillator 16 operates at the resonant frequency of resonator 32, two conditions characteristic of the stable operation of any oscillator must be satisfied. First, the closed-loop gain of the circuit defined by the oscillator 16 and resonator 32 must be equal to unity. Addressing this condition in greater detail, the circuit shown in FIG. 2 can be considered to include a forward network 38 and a feedback network 40. The forward network 38 includes an amplifier 42 that amplifies the output $V_1$ of feedback network 40 by a complex, frequency-dependent gain A to produce an output voltage $V_0$. The feedback network 40 includes the resonator 32 and feedback elements 46. The feedback network 40 is characterized by a complex, frequency-dependent transfer function $\beta$ and produces the output $V_1$, which is equal to the product of voltage $V_0$ and the transfer function $\beta$.

The loop gain of the circuit in FIG. 2 is equal to the product of the terms A and $\beta$. As this loop gain approaches $+1$, the ratio of the circuit's output voltage to its input voltage approaches infinity, allowing the circuit to oscillate or produce an output even when no input is applied. Both A and $\beta$ are complex, frequency-dependent quantities that can be expressed in polar form as an amplitude and an angle. Because oscillation can take place only if the vector product of A and $\beta$ is $+1$, the product of the amplitudes of A and $\beta$ must be equal to $+1$, while the sum of the angles of A and $\beta$ must equal 0. This latter characteristic defines the second requirement for oscillation, which is that the loop phase shift must be equal to 0 or some multiple of 360 degrees.

Discussing the various components of the basic circuit of FIG. 2 in greater detail, resonator 32 can be considered to include four elements. As noted previously, the equivalent circuit 34, representative of site 12, electrodes 14, and gaps 30, includes a series capacitance C1 and resistance R1. The portion of C1 attributable to the gaps 30 is relatively large and variable, leading to fluctuations in the resonant frequency of resonator 32. The equivalent series resistance R1 includes the resistance inherent in the living tissue, which is on the order of 100 ohms. This resistance R1 also includes the effective series resistance associated with the forward network 38 and feedback network 40, as well as the losses in the series inductor L1. This latter component may be made relatively small by carefully designing the inductor L1 to provide a high quality factor Q.

As shown in FIG. 2, resonator 32 also includes a capacitor C2 connected in series with equivalent circuit 32. Capacitor C2 prevents oscillator 16 from operating in spurious and multiple high-frequency modes by introducing a high-frequency roll-off into the feedback network 42. The capacitance (e.g., 10 nF) of capacitor C2 is typically much greater than that of C1. One end of capacitor C2 is coupled to ground, while the other end is connected directly to equivalent circuit 34 and by feedback to the forward network 38. The series inductor L1 is included in resonator 32 to reduce the dissipation of energy from the electric field established between electrodes 14 by receiving most of the stored energy of the field and returning it during the next cycle of the alternating potential applied to the electrodes 14. Inductor L1 typically has an inductance on the order of 100 mH.

Turning now to a discussion of the forward network 40, network 40 preferably includes a source 42 that provides a low-impedance output voltage to resonator 32. The voltage source 42 also preferably operates in a switching mode for enhanced efficiency. A suitable source or amplifier 42 is a complementary, metal-oxide-semiconductor inverter of the type manufactured by Motorola under the designations MC14049UB or MC14069UB. Such an amplifier 42 provides a square wave output and introduces a phase shift of approximately 180 degrees into the loop at the desired operating frequency of around 50 kilohertz.

Forward network 40 also includes a resistor R2. As noted previously, at resonance, the capacitive and inductive reactances have a cancellative effect on each other, exerting no influence on the amplitude of the current flowing through resonator 32. As a result, the therapeutic current induced at the patient site 12 can be controlled either by altering the voltage applied to resonant circuit 32 or its series resistance. The resistor R2 is connected in series with the equivalent resistance R1 of resonator 32 to regulate the therapeutic current to the desired level. Preferably, R2 has a resistance (e.g., 750 ohms) that is sufficient to increase the total series resistance of the circuit to approximately 1000 ohms. As will be discussed in greater detail below, with a compact, 9-volt battery for source 20 and the 4049-type inverter 42 employed in forward network 40, an oscillator output of approximately 5 volts rms is achieved, providing a normally desired therapeutic current of 5 milliamperes at resonance.

As shown in FIG. 2, feedback network 40 includes both the resonator 32 and feedback elements 46. Feedback elements 46 provide the loop with the desired unity gain and zero phase shift characteristics. While elements 46 could be merged with the forward network 38, both in theory and in practice, they are shown separately in FIG. 2 to assist in an understanding of the circuit.

As represented in FIG. 2, the feedback elements 46 include an amplifier 48 and phase lag 50, which ensure that the complex transfer function $\beta$ of the feedback network 40 satisfies the loop's unity gain and zero phase shift requirements. Specifically, the gain provided by amplifier 48 compensates for both the gain of amplifier 42 and the attenuation introduced by resonator 32. Regarding phase shift, the current flowing through the resonator 32 is in phase with the voltage at the output of the forward network 38 at resonance. This current produces a voltage across capacitor C2 having a phase that lags that of the output voltage from amplifier 42 by 90 degrees. Assuming that amplifiers 42 and 48 introduce a phase shift of 270 degrees into the loop, phase lag 50 is required to provide the remaining 90 degrees of shift. As a result, 360 degrees of phase shift is produced, allowing stable oscillation.

To ensure that oscillator 16 will oscillate at start-up, the combined gain of amplifiers 42 and 48 is designed to exceed any voltage attenuation introduced by the resonator 32 and phase shifter 50. The unity gain condition for stable oscillation of the loop is satisfied by making at least one of the amplifiers 42 or 48 saturable. With a 4049-type device employed for amplifier 42, such saturation is inherent.

Figure 3:
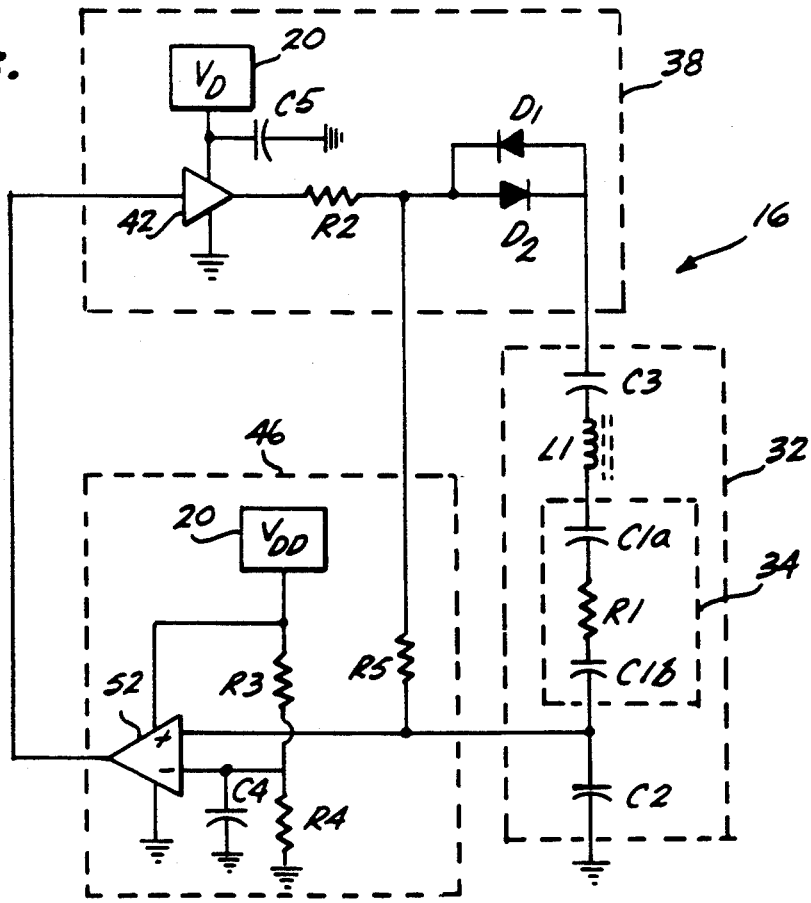
FIG. 3 is a more detailed schematic diagram of the embodiment of the oscillator circuit shown in FIG. 2.

FIG. 3 illustrates, in slightly greater detail, a preferred embodiment of the system 10 of FIG. 2. Addressing first the resonator 32, the capacitor C1 of FIG. 2 has been depicted as two capacitors $C1_a$ and $C1_b$ in FIG. 3. The capacitance of element $C1_a$ corresponds to that of the electrodes 14 and gaps 30, while capacitor $C1_b$ is representative of site 12.

The series resonant circuit 32 of FIG. 3 also includes an additional capacitor C3, having a capacitance on the order of 220 picofarads. While the inclusion of this capacitor C3 is not essential, it assures oscillation of system 10, regardless of the normal variations of capacitance of elements $C1_a$ and $C1_b$. As will be appreciated, the series capacitance of elements $C1_a$ and $C1_b$ may become very large and even representative of a virtual short circuit when, for example, the patient is perspiring heavily and the electrodes 14 are spaced apart from the patient by only a woven cotton sleeve designed to "wick" perspiration from the site. As a result of this increase in capacitance, the resonant frequency of resonator 32 could shift sufficiently to prevent oscillator 16 from achieving a unity loop gain or zero phase shift and, hence, oscillation. By adding a capacitor C3 whose capacitance is preferably on the order of four times that of the nominal value of the series combination of capacitors $C1_a$ and $C1_b$, the resonant frequency of resonator 32 cannot drop to less than approximately one-half its nominal value and oscillation is assured. It is also preferable to use the additional capacitor C3 to prevent the possible flow of direct current through the electrode circuit. Such flow might have adverse consequences through electrolytic action, especially in the presence of moisture on the electrodes.

FIG. 3 also includes additional details regarding the construction of the feedback elements 46. As noted previously, this portion of network 42 is designed to satisfy the zero phase shift and unity gain requirements of oscillation by introducing a 90-degree phase lag into the circuit, as well as sufficient gain to overcome the loss introduced by the resonator 32. Both functions are conveniently provided by an operational amplifier 52 connected "open-loop" or without feedback. The operational amplifier 52 should have a sufficient open-loop gain over the range of expected operating frequencies to make the oscillator loop gain equal to unity without depending upon amplifier 42 for gain. A suitable operational amplifier 52 is provided by any one of the four operational amplifiers included in the integrated circuit device manufactured by Texas Instruments under the part designation TLC27M4. This device is available with internal compensation to provide a 90-degree phase shift over a wide frequency range, including the desired operating frequency of approximately 50 kilohertz.

The inverting input of the operational amplifier 52 is coupled to a voltage divider formed by the series combination of resistors R3 and R4. More particularly, one end of resistor R3 is coupled to the supply 20, one end of resistor R4 is coupled to ground, and the connection of resistors R3 and R4 is coupled to the inverting input. Because both resistors R3 and R4 have a resistance that is on the order of 100 kilohms, a voltage equal to approximately one-half the supply 20 voltage $V_{dd}$ is applied to the inverting input. The inverting input of operational amplifier 52 is also coupled to ground by a bypass capacitor C4 having a capacitance of 100 nF and the noninverting input is coupled to the resonator 32 at the ungrounded side of capacitor C2.

DC negative feedback is introduced into the oscillator circuit by a resistor R5. Resistor R5 is coupled between the noninverting input of operational amplifier 52 and the output of the amplifier 42 in forward network 38, as shown in FIG. 3. Resistor R5 has a resistance of approximately 100 kilohms and is included to ensure the initiation of oscillation by placing amplifiers 42 and 52 within their common-mode ranges at start-up.

Turning finally to a more detailed discussion of the forward network 38, as discussed previously it preferably employs a complementary metal-oxide-semiconductor inverter for amplifier 42. The amplifier is driven rail-to-rail at the voltage $V_{dd}$ provided by supply 20 to enhance efficiency and is also coupled to a bypass capacitor C5 having a capacitance of approximately 100 nF.

As noted previously, resistor R2 is included in the forward network 38 and has a resistance that is sufficient to provide the desired therapeutic current level for the particular output produced by amplifier 42. A pair of reverse, parallel-connected light-emitting diodes D1 and D2, such as those manufactured by Texas Instruments under the part number TIL213-2 are included in series with resistor R2. The diodes D1 and D2 output an easily observable quantity of light when energized at the therapeutic current level of approximately 5 milliamperes rms. As a result, the light-emitting diodes D1 and D2 directly indicate the application of therapeutically effective current to the site 12, rather than simply indicating that circuit power is available to establish such a current. This advantageously avoids the production of an output if oscillation ceases due to the failure of a component or an improper spacing of the electrodes 14.

Because each light-emitting diode D1 and D2 only passes current in one direction, the reverse, parallel connection of diodes D1 and D2 is employed to accommodate the alternating current established in the resonant circuit 32. The forward drop of diodes D1 and D2 is on the order of one volt. As a result, the effective voltage applied to resonator 32 is reduced, requiring that the resistive value of resistor R1 be adjusted accordingly to maintain the desired level of therapeutic current.

Figure 4:
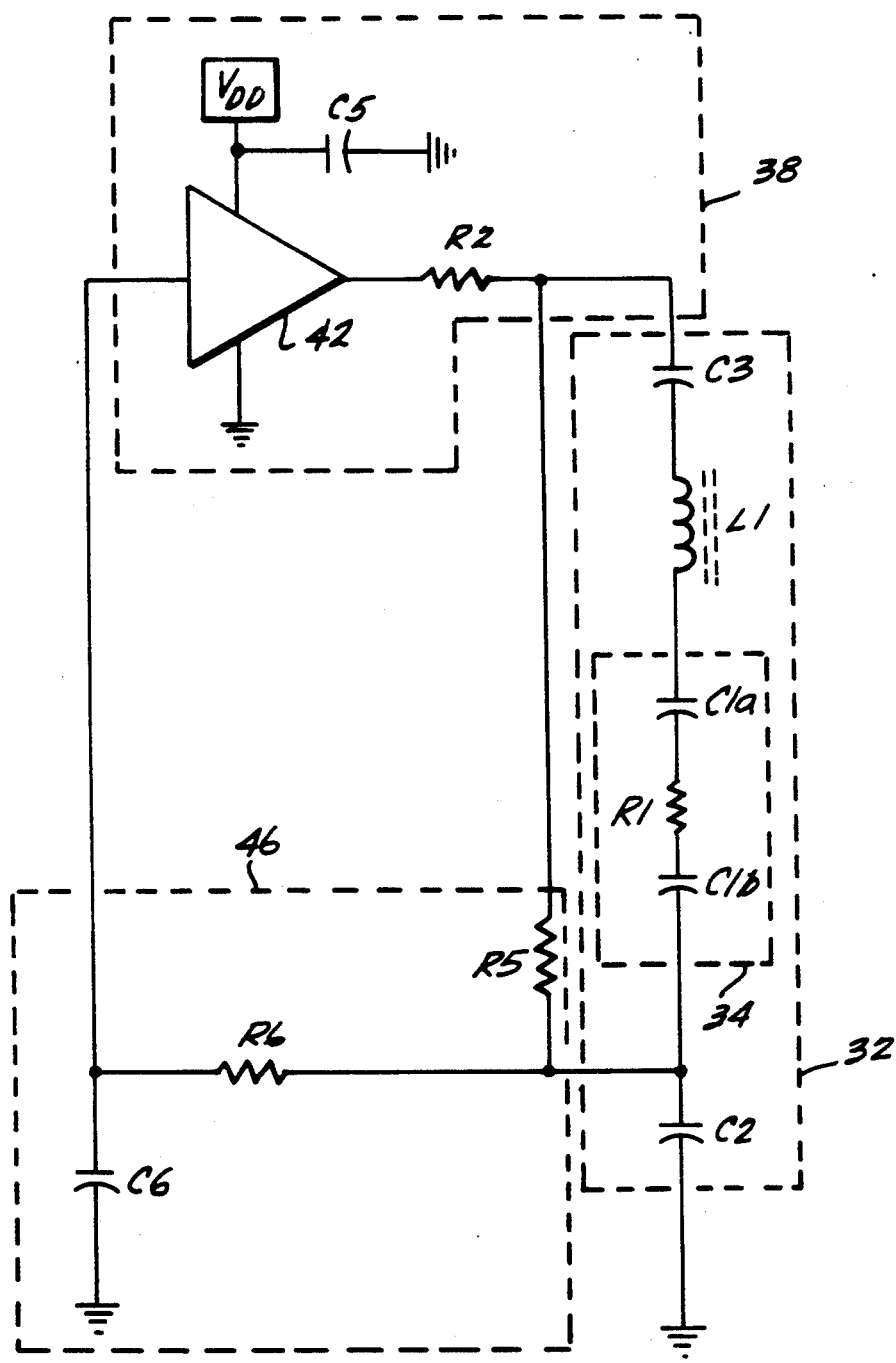
FIG. 4 is a schematic diagram of a second embodiment of the oscillator circuit of FIG. 2.

As will be appreciated, a number of modifications can be made to the oscillator circuit 16 of FIG. 3. For example, as shown in FIG. 4, the active operational amplifier 52 can be removed from the circuit and a resistor R6 and capacitor C6 employed as the feedback elements 46. With capacitor C2 exhibiting a high reactance, for example, at a capacitance of 1 nanofarad, the voltage across capacitor C2 will remain relatively high. Thus, even after being attenuated by the combination of resistor R6 and capacitor C6, the voltage will still be sufficient to drive amplifier 42. The combination of resistor R6 and capacitor C6 also produces the desired phase shift of approximately 90 degrees for all frequencies that are attenuated by roughly a tenfold factor or more.

Another modification relates to the use of amplifier 42. While a single amplifier 42 is shown in the schematic diagram of FIG. 3, a number of such elements are normally connected in parallel to achieve an internal series resistance that is relatively low in comparison to that of R2. As will be appreciated, the amplifier resistance is heavily dependent upon ambient temperature and varies from unit to unit in a production run. Because the series resistance of the circuit directly affects current level, the resistance of resistor R2 should always be dominant if the therapeutic current level is to be accurately maintained.

Turning now to a discussion of the remaining elements of control and output subsystem 18, as noted previously, a 9-volt battery may conveniently be employed for power supply 20. The use of such a battery not only ensures the absence of any high-voltage failure modes, it also contributes to the relative portability of system 10, which may be particularly desirable when system 10 is mounted to a patient's cast for extended periods of use.

Because the level of therapeutic current induced at site 12 is a function, in part, of the voltage applied to resonator 32, it is important that supply 20 maintains a sufficient voltage for availability to oscillator 16. In this regard, a power supply voltage output 28 is included to provide an output indicative of the status of supply 20. For example, a simple direct current voltmeter could be employed for output 28 to indicate the voltage available from supply 20. Alternatively, output 28 could include a comparator having the battery voltage as one input, a threshold voltage as another input, and an output coupled to an audible or visual alarm when the battery voltage drops below the threshold.

Subsystem 18 also includes a timer 22 designed to sequence oscillator 16 on and off at desired intervals. More particularly, with empirical studies conducted to determine the cycling rate resulting in the production of an optimal therapeutic effect, timer 22 can then be set to cycle oscillator 16 on and off at that rate. In addition, timer 22 can be set to initiate and interrupt this cycled operation at desired times.

As will be appreciated, various constructions can be employed for timer 22, depending on the particular operation desired. For example, if an adjustable start time, stop time, and cycle rate are desired, along with the ability to retain output information regarding the treatment period, a microprocessor-based timer 22 programmed with an appropriate set of operating instructions may be useful. In this manner, a timing pulse output 26 can easily be provided, displaying information indicative of the number of timing pulses applied to oscillator 16, for analysis by the physician. Alternatively, output 26 can be a simple counter.

As noted previously, the visual display 24 preferably includes a pair of reverse, parallel-connected, light-emitting diodes D1 and D2, which directly indicate the establishment of a therapeutic current at the site 12. As will be appreciated, with timer 22 set to cycle oscillator on for one second and off for two seconds, as an example, diodes D1 and D2 will appear to be lit and extinguished for corresponding intervals. In a preferred arrangement employing an appropriately programmed, microprocessor-based timer 22, when a low voltage is sensed at supply 20, the cycle rate produced by timer 22 can be altered to provide a change in the display produced by diodes D1 and D2 indicating a low-battery condition.

The system 10 constructed in the manner described above has a number of advantages. For example, the system 10 induces the desired therapeutic current at the patient site 12 in a straightforward manner with relatively few components. The system 10 is also stable, rejects high-frequency spurious oscillations, and produces an output directly indicating the establishment of a therapeutic current at the treatment site 12.

Another advantage of system 10 is that it enhances patient safety by avoiding the application of a high-voltage drive output directly to the electrodes 14. More particularly, with a constant drive voltage employed, the current established at the treatment site 12 varies in inverse proportion to the capacitive reactance of the equivalent circuit 34. In certain circumstances, for example, when electrodes 14 come into direct contact with the skin of a heavily perspiring patient, the capacitive reactance may be negligible, resulting in the production of a large and potentially injurious "fault" current.

The disclosed system 10 overcomes this difficulty by providing a drive voltage that is limited, in case of direct electrode-to-skin contact, to the relatively low voltage $V_{dd}$ of the supply 20, for example, 9 volts. As a result, system 10 has no high-voltage failure modes. Further, the drive current is limited by resistor R2, which may be a series of several resistors or a single resistor constructed to have only an open-circuit failure mode. In no circumstance will any failure of an active component result in an over-current condition hazardous to the patient.

Those skilled in the art will recognize that the embodiments of the invention disclosed herein are exemplary in nature and that various changes can be made therein without departing from the scope and spirit of the invention. In this regard, and as was previously mentioned, the invention is readily embodied with either active or passive components in the feedback network to provide the desired unity loop gain in zero phase shift. Further, it will be recognized that a variety of active elements can be employed in the forward and feedback networks. Because of the above and numerous other variations and modifications that will occur to those skilled in the art, the following claims should not be limited to the embodiments illustrated and disclosed herein.

The embodiments of the invention in which an exclusive property or privilege is claimed are defined as follows:

1. An apparatus for applying an electric current to a region of a patient through a pair of electrodes positionable in noncontacting relationship with respect to the patient, the region of the patient and any gaps between the patient and the electrodes exhibiting a series capacitance and resistance, said apparatus comprising:
   inductive means, coupleable to one of the electrodes, for defining a resonator in cooperation with the series capacitance and resistance;
   oscillation means, coupled to said inductive means, for providing to said resonator a periodic current whose frequency is substantially equal to the resonant frequency of said resonator; and
   means for limiting the occurrence of spurious oscillation frequencies in said periodic current provided by said oscillation means.

2. The apparatus of claim 1, wherein said oscillation means defines a closed loop with said resonator and further comprises first section means, for providing a first amplitude adjustment and first phase shift to signals conducted by said loop, and second section means, for providing a second amplitude adjustment and second phase shift to signals conducted by said loop, said closed loop having a gain of unity and a phase shift equivalent to zero degrees.

3. The apparatus of claim 2, wherein said means for limiting the occurrence of spurious oscillation frequencies is a capacitive element further defining said resonator in cooperation with said inductive means and said series capacitance and resistance, said capacitive element introducing an approximately 90-degree phase shift into said loop.

4. The apparatus of claim 1, further comprising means for cycling said oscillation means between periods during which said resonator current is provided and is not provided.

5. The apparatus of claim 4, further comprising means for producing an output indicative of the number of periods said osciallation means is cycled through.

6. The apparatus of claim 1, wherein said apparatus further comprises a voltage source for operably powering said oscillation means and means for indicating whether the voltage available from the source has dropped below some predetermined level.

7. The apparatus of claim 1, further comprising visual output means for producing a visual output indicative of the provision of said periodic current to said resonator.

8. A method of applying an electric current to a region of a patient through a pair of electrodes positionable in noncontacting relationship with respect to the patient, the region of the patient and any gaps between the patient and the electrodes exhibiting a series capacitance and resistance, the method comprising the steps of:
   forming a resonator including the series capacitance and resistance;
   providing to said resonator a periodic current whose frequency is substantially equal to the resonant frequency of said resonator; and
   limiting the occurrence of spurious oscillation frequencies in said periodic current provided to said resonator.

9. The method of claim 8, further comprising the step of producing an output indicative of the provision of said periodic current when said periodic current is provided to said resonator.

10. An apparatus for applying an electric current to a region of a patient through a pair of electrodes positionable in noncontacting relationship with respect to the patient, the region of the patient and any gaps between the patient and the electrodes exhibiting a series capacitance and resistance, said apparatus comprising:

inductive means, coupleable to one of the electrodes, for defining a resonator in cooperation with the series capacitance and resistance; and feedback means, coupled to said inductive means, for providing to said resonator a periodic current that has not undergone inductive transformation and whose frequency is substantially equal to the resonant frequency of said resonator.

11. A circuit for efficiently applying an electric current to a region of a patient through a pair of electrodes positionable in noncontacting relationship with respect to the patient, the region of the patient any gaps between the patient and the electrodes exhibiting a variable series capacitance and resistance, said circuit consisting of:

inductive means, coupleable to one of the electrodes and having a fixed inductance, for defining a resonator in cooperation with the series capacitance and resistance;

power supply means for providing a power supply output;

amplification means for receiving the power supply output and amplifying the electric current;

phase adjustment means for adjusting the phase of the electric current, said amplification means and said phase adjustment means defining a loop with the resonator through which the electric current flows, the amplification performed by said amplification means and the phase adjustment performed by said phase adjustment means causing said loop to exhibit unity gain and effectively zero phase shift and to maintain the frequency of said electric current equal to the resonant frequency of said resonator substantially independent of variations in the capacitance of gaps between the patient and the electrodes.

* * * * *